(12) United States Patent
Kapadia et al.

(10) Patent No.: US 12,029,521 B2
(45) Date of Patent: Jul. 9, 2024

(54) SURGICAL ROBOTIC SYSTEMS

(71) Applicant: Covidien LP, Mansfield, MA (US)

(72) Inventors: Jaimeen Kapadia, Cambridge, MA (US); Ranjan Mishra, Orange, CT (US)

(73) Assignee: COVIDIEN LP, Mansfield, MA (US)

( * ) Notice: Subject to any disclaimer, the term of this patent is extended or adjusted under 35 U.S.C. 154(b) by 600 days.

(21) Appl. No.: 17/270,731

(22) PCT Filed: Sep. 10, 2019

(86) PCT No.: PCT/US2019/050269
§ 371 (c)(1),
(2) Date: Feb. 23, 2021

(87) PCT Pub. No.: WO2020/060791
PCT Pub. Date: Mar. 26, 2020

(65) Prior Publication Data
US 2021/0212786 A1    Jul. 15, 2021

Related U.S. Application Data

(60) Provisional application No. 62/732,192, filed on Sep. 17, 2018.

(51) Int. Cl.
*F16H 47/00* (2006.01)
*A61B 17/00* (2006.01)
(Continued)

(52) U.S. Cl.
CPC ........ *A61B 34/74* (2016.02); *A61B 17/00234* (2013.01); *A61B 34/37* (2016.02); *A61B 2017/00477* (2013.01)

(58) Field of Classification Search
CPC ... A61B 34/74; A61B 17/00234; A61B 34/37; A61B 2017/00477; A61B 2034/302
See application file for complete search history.

(56) References Cited

U.S. PATENT DOCUMENTS

2010/0175701 A1   7/2010 Reis et al.
2011/0040150 A1   2/2011 Govari et al.
(Continued)

FOREIGN PATENT DOCUMENTS

CN    108158656 A    6/2018
FR    3109481    * 10/2021    ............... H02K 1/12
(Continued)

OTHER PUBLICATIONS

Translation of FR 3109481, Foucaut et al., Oct. 22, 2021 (Year: 2021).*

(Continued)

*Primary Examiner* — Vinh Luong
(74) *Attorney, Agent, or Firm* — Carter, DeLuca & Farrell, LLP

(57) ABSTRACT

An instrument drive unit for use in a robotic surgical system includes a carriage configured to be coupled to a robotic arm, a plurality of drive shafts rotationally supported in the carriage, a plurality of electric motors disposed about the plurality of drive shafts, and a plurality of drive gears. Each electric motor includes a stator and a rotor disposed within the stator. Each drive gear is fixed to a corresponding drive shaft and is configured for interfacing with a corresponding driven member of the electromechanical surgical instrument. Each rotor is configured to rotate a corresponding drive gear in response to an activation of a respective electric motor to actuate a function of the electromechanical surgical instrument.

18 Claims, 3 Drawing Sheets

(51) Int. Cl.
  *A61B 34/00* (2016.01)
  *A61B 34/37* (2016.01)
  *B25J 9/10* (2006.01)
  *F16D 37/02* (2006.01)

(56) References Cited

U.S. PATENT DOCUMENTS

| | | |
|---|---|---|
| 2012/0247268 A1 | 10/2012 | Viola |
| 2015/0094732 A1 | 4/2015 | Pacheco et al. |
| 2016/0066982 A1 | 3/2016 | Marczyk et al. |
| 2016/0374769 A1 | 12/2016 | Schena et al. |
| 2017/0135773 A1 | 5/2017 | Lohmeier et al. |
| 2017/0273749 A1 | 9/2017 | Grover et al. |
| 2018/0133905 A1* | 5/2018 | Smith ................ F16D 25/048 |
| 2018/0168748 A1* | 6/2018 | Kapadia ................ A61B 17/29 |
| 2019/0239966 A1* | 8/2019 | Xu ........................ A61B 34/71 |
| 2020/0253676 A1* | 8/2020 | Traina ................... A61B 34/30 |
| 2021/0154830 A1* | 5/2021 | Lee ......................... B25J 9/102 |
| 2021/0220063 A1* | 7/2021 | Kapadia ..................... B25J 9/12 |
| 2021/0282814 A1* | 9/2021 | Prior ................ A61B 17/4241 |
| 2021/0338347 A1* | 11/2021 | Kapadia ................ A61B 34/70 |
| 2021/0393340 A1* | 12/2021 | Beckman ............... A61B 90/50 |
| 2022/0125529 A1* | 4/2022 | Kapadia ................ A61B 17/00 |
| 2023/0098877 A1* | 3/2023 | Plante .................... F16H 47/00 74/89.13 |

FOREIGN PATENT DOCUMENTS

| | | | |
|---|---|---|---|
| WO | WO 2016043845 A1 * | 3/2016 | ............. A61B 19/00 |
| WO | 2018041204 A1 | 3/2018 | |
| WO | WO 2019012431 A1 * | 1/2019 | ............. B25J 18/04 |
| WO | 2020009831 A1 | 1/2020 | |

OTHER PUBLICATIONS

International Search Report dated Dec. 27, 2019, issued in corresponding international application No. PCT/US2019/050269, 9 pages.

Extended European Search Report dated May 16, 2022, issued in corresponding EP Application No. 19862230, 11 pages.

* cited by examiner

SURGICAL ROBOTIC SYSTEMS

BACKGROUND

Surgical robotic systems have been used in minimally invasive medical procedures. Some surgical robotic systems included a console supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

The instrument drive unit was typically coupled to the robotic arm via a slide. The slide allowed the instrument drive unit and the attached surgical instrument to move along an axis of the slide, providing a means for adjusting the axial position of the end effector of the surgical instrument.

SUMMARY

In accordance with an aspect of the present disclosure, an instrument drive unit for use in a robotic surgical system is provided and includes a carriage configured to be coupled to a robotic arm, a plurality of drive shafts rotationally supported in the carriage, a plurality of electric motors disposed about the plurality of drive shafts, and a plurality of drive gears. Each electric motor includes a stator and a rotor disposed within the stator. Each drive gear is fixed to a corresponding drive shaft and is configured for interfacing with a corresponding driven member of the electromechanical surgical instrument. Each rotor is configured to rotate a corresponding drive gear in response to an activation of a respective electric motor to actuate a function of the electromechanical surgical instrument.

In aspects, each stator may be fixed relative to the carriage, and each rotor may be rotatable relative to and within a corresponding stator.

In other aspects, the electrical motors may be vertically stacked within the carriage.

In some aspects, the instrument drive unit may further include a sleeve rotationally coupled to a distal end portion of the carriage. The sleeve may be configured to non-rotationally retain the electromechanical surgical instrument.

In an aspect, the instrument drive unit may include a drive motor having a stator fixed within the carriage, and a rotor disposed within the stator of the drive motor and non-rotatably coupled to the sleeve. The rotor of the drive motor may be configured to rotate the sleeve about a central longitudinal axis defined by the carriage.

In aspects, the instrument drive unit may further include a plurality of ring gears. Each ring gear may be fixed to a corresponding rotor and operably coupled to a corresponding drive gear.

In some aspects, each ring gear may be concentrically disposed within a corresponding rotor, such that rotation of the rotor results in a rotation of the corresponding ring gear.

In other aspects, the ring gears may be vertically stacked within the electric motors.

In an aspect, a first electric motor, a first ring gear, and a first drive gear may be operably coupled to one another and aligned along a first plane.

In aspects, a second electric motor, a second ring gear, and a second drive gear may be operably coupled to one another and aligned along a second plane, vertically displaced from the first plane.

In some aspects, the ring gears may be independently rotatable relative to one another.

In other aspects, a first ring gear may have gear teeth on an inner periphery thereof. The gear teeth on the inner periphery of the first ring gear may interface with a corresponding drive gear, and an outer periphery of the first ring gear may be attached to an inner periphery of a corresponding rotor.

In an aspect, the drive gears may be vertically offset from one another.

In aspects, each drive shaft may have a distal end portion configured for interfacing with a corresponding driven member of the electromechanical surgical instrument.

In some aspects, each drive shaft may have a series of idler gears rotatably disposed thereabout and vertically offset from one another. The series of idler gears may interface with a corresponding ring gear to stabilize the drive shafts within the electric motors.

In another aspect of the present disclosure, an instrument drive unit for use in a robotic surgical system is provided and includes a carriage configured to be coupled to a robotic arm, a plurality of electric motors supported in the carriage, and a plurality of drive shafts disposed within the plurality of electric motors. Each electric motor includes a stator and a rotor disposed within the stator. The drive shafts are configured for interfacing with a corresponding driven member of an electromechanical surgical instrument. Each drive shaft has a drive gear fixed thereabout. The drive gears are disposed at a discrete vertical location relative to one another. Each rotor is configured to rotate a corresponding drive gear in response to an activation of a respective electric motor of the plurality of electric motors to actuate a function of the electromechanical surgical instrument.

In some aspects, the instrument drive unit may further include a plurality of vertically stacked ring gears. Each ring gear is fixed to a corresponding rotor and operably coupled to a corresponding drive gear, such that each rotor is configured to rotate a corresponding drive gear in response to an activation of a respective electric motor of the plurality of electric motors to actuate a function of the electromechanical surgical instrument.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
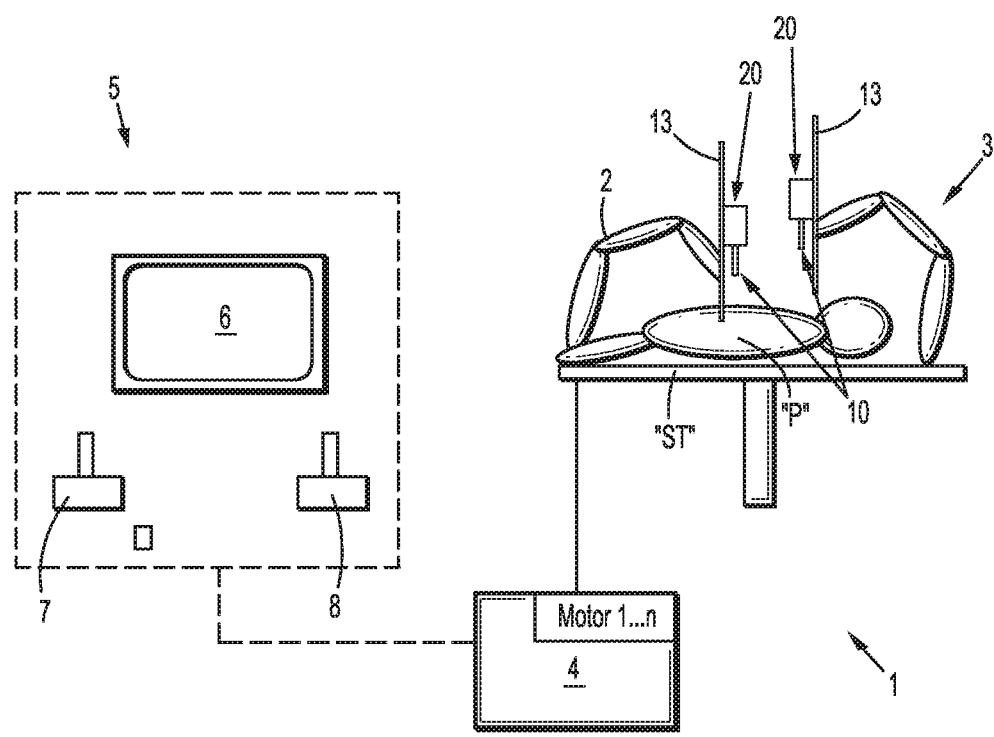
FIG. 1 is a schematic illustration of a surgical robotic system including an instrument drive unit coupled to a slide in accordance with the present disclosure.
Figure 2:
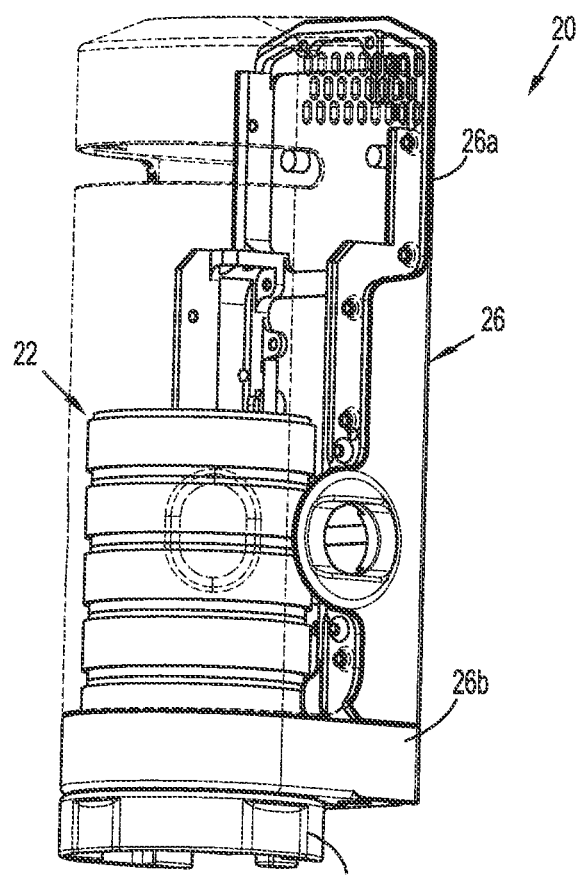
FIG. 2 is a perspective view of the instrument drive unit of the surgical robotic system of FIG. 1 with parts of a carriage of the instrument drive unit shown in phantom, illustrating internal components of the instrument drive unit.

Embodiments of the presently disclosed surgical robotic system and instrument drive units thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient. As used herein, the term "vertical" refers to a direction defined along a longitudinal axis of a portion of the surgical robotic system, while the term "horizontal" refers to a direction defined along a transverse axis of a portion of the surgical robotic system.

As will be described in detail below, provided is an instrument drive unit of a surgical robotic system configured to allow for a bottom-loading of a surgical instrument. The instrument drive unit has a plurality of drive shafts each configured to be coupled to a corresponding driven member of the surgical instrument for carrying out a discrete function of the surgical instrument. The drive shafts of the instrument drive unit are operably coupled to a discrete electric motor of the instrument drive unit via a discrete transmission assembly. The configuration of the transmission assemblies allows for a reduction in the overall height of the instrument drive unit (e.g., the instrument drive unit is more compact). For example, gears of the transmission assemblies are vertically and horizontally offset from the gears of the other transmission assemblies. Other features and benefits of the disclosed instrument drive units are further detailed below.

Referring initially to FIG. 1, a surgical system, such as, for example, a surgical robotic system 1, generally includes a plurality of surgical robotic arms 2, 3; an elongated slide 13 coupled to an end of each of the robotic arms 2, 3; an instrument drive unit 20 and an electromechanical instrument 10 removably attached to the slide 13 and configured to move along the slide 13; a control device 4; and an operating console 5 coupled with control device 4. The operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached instrument drive units 20, and thus electromechanical instrument 10 execute a desired movement according to a movement defined by means of manual input devices 7, 8. Control device 4 may also be set up in such a way that it regulates the movement of the instrument drive unit 20 along the slide 13, movement of the robotic arms 2, 3, and/or movement of the drives.

Surgical robotic system 1 is configured for use on a patient "P" lying on a surgical table "ST" to be treated in a minimally invasive manner by means of a surgical instrument, e.g., electromechanical instrument 10. Surgical robotic system 1 may also include more than two robotic arms 2, 3, the additional robotic arms likewise being connected to control device 4 and being telemanipulatable by means of operating console 5. A surgical instrument, for example, an electromechanical surgical instrument 10 (including an electromechanical end effector), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of electric motors 22 (FIGS. 2-5) of the instrument drive unit 20 to drive various operations of the surgical instrument 10. The instrument drive unit 20 transfers power and actuation forces from its motors to driven members (not shown) of the electromechanical instrument 10 to ultimately drive movement of components of the end effector of the electromechanical instrument 10, for example, a movement of a knife blade (not shown) and/or a closing and opening of jaw members of the end effector.

For a detailed description of the construction and operation of a robotic surgical system, reference may be made to U.S. Pat. No. 8,828,023, entitled "Medical Workstation," the entire contents of which are incorporated by reference herein.

With reference to FIGS. 2-5, the instrument drive unit 20 will now be described in detail. The instrument drive unit 20 includes a carriage 26 and a coupling or sleeve 28 rotatably coupled to a distal end portion 26b of the carriage 26 for connecting a surgical instrument 10 (FIG. 1) to the instrument drive unit 20. The carriage 26 of the instrument drive unit 20 is configured to be slidably coupled to a linear track (not shown) defined longitudinally along the slide 13 (FIG. 1). A proximal end portion 26a of the carriage 26 houses a plurality of electric motors 22a, 22b, 22c, 22d, 22d, 22e (collectively referred to herein as "22") for carrying out various functions of an attached surgical instrument 10.

The electric motors 22 of the instrument drive unit 20 are concealed within the carriage 26. The electric motors 22 are vertically stacked on one another and are independently actuatable via the control device 4 (FIG. 1). One of the electric motors, such as, for example, the fifth electric motor 22e, is configured to effectuate a rotation of the surgical instrument 10 when the surgical instrument 10 is coupled to the instrument drive unit 20, and the remaining electric motors 22a, 22b, 22c, 22d are configured to actuate functions of the surgical instrument 10, as will be described. The electric motors 22 are integrated AC motors. In embodiments, the electric motors 22 may be any suitable type of electric motor such as an AC brushless motor, a DC brushed motor, a DC brushless motor, a direct drive motor, a servo motor, a stepper motor, or the like. It is contemplated, and within the scope of the present disclosure, that electric motors 22 are in the form of hollow core motors, or the like. Other types of motors are also contemplated. While the instrument drive unit 20 is illustrated as having five electric motors, it is contemplated that the instrument drive unit 20 may have more or less than five electric motors. The electric motors 22 are interlinked, thereby providing an infinite range of motion along the longitudinal axis "X" of the instrument drive unit 20.

Figure 3:
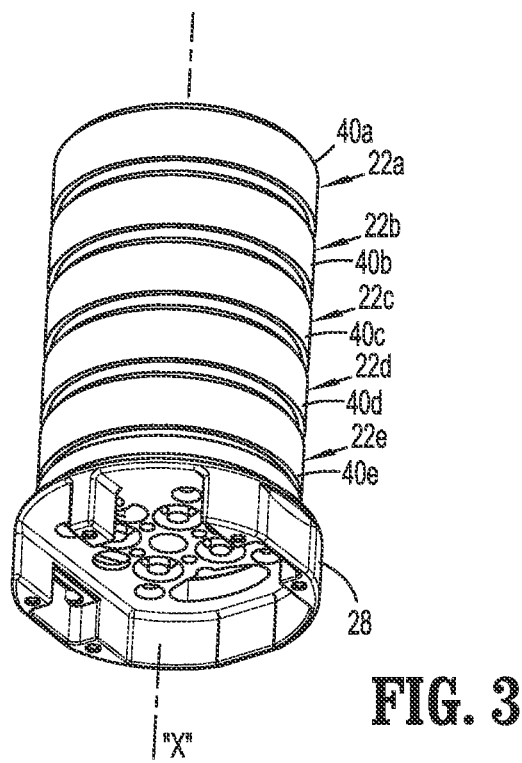
FIG. 3 is a front, perspective view of a series of vertically stacked electric motors of the instrument drive unit of FIG. 2.
Figure 4:
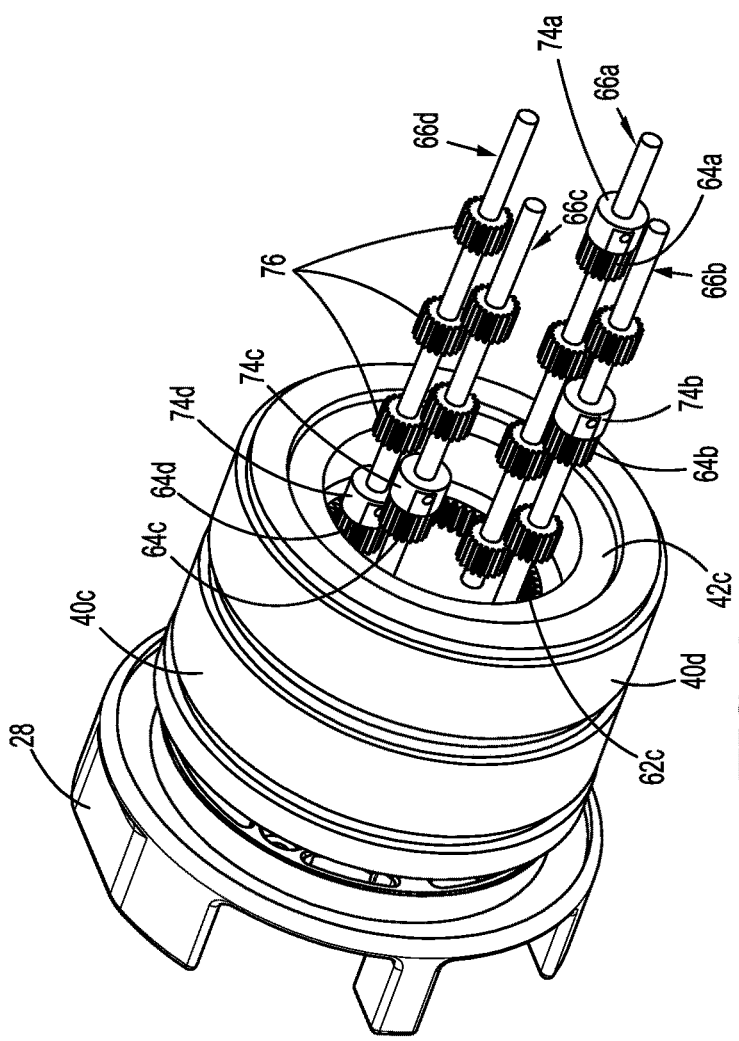
FIG. 4 is a perspective view, with some of the electric motors and rings gears removed, thereby revealing a plurality of drive shafts of the instrument drive unit.

The electric motors 22 each have a stator 40a, 40b, 40c, 40d, 40e (collectively referred to herein as "40") fixed within the carriage 26, and a rotor 42 (only rotors 42a, 42d are illustrated) rotationally disposed within a corresponding stator 40. Each of the stators 40 may be annularly shaped and stacked on top of one another to form a hollow cylinder, as best shown in FIG. 3. The stators 40 may be configured to receive an electric current from a power source (not explicitly shown) to produce a rotating magnetic field that drives a rotation of the rotors 42.

Each of the rotors 42 may be configured as a permanent magnetic, an electromagnet, or any other suitable conductor. The rotors 42 are vertically stacked within the hollow cylinder formed by the stators 40 and are independently rotatable relative to one another about a central longitudinal axis "X" defined by the motors 22.

With continued reference to FIGS. 2-5, the instrument drive unit 20 further includes a plurality of ring gears 62a, 62d, a plurality of drive gears 64a, 64b, 64c, 64d (collectively referred to herein as "64"), and a plurality of drive shafts 66a, 66b, 66c, 66d (collectively referred to herein as "66"). While only ring gears 62a and 62d are illustrated, the instrument drive unit 20 has four ring gears for coupling the four drive gears 64 and the corresponding four rotors 42.

Figure 5:
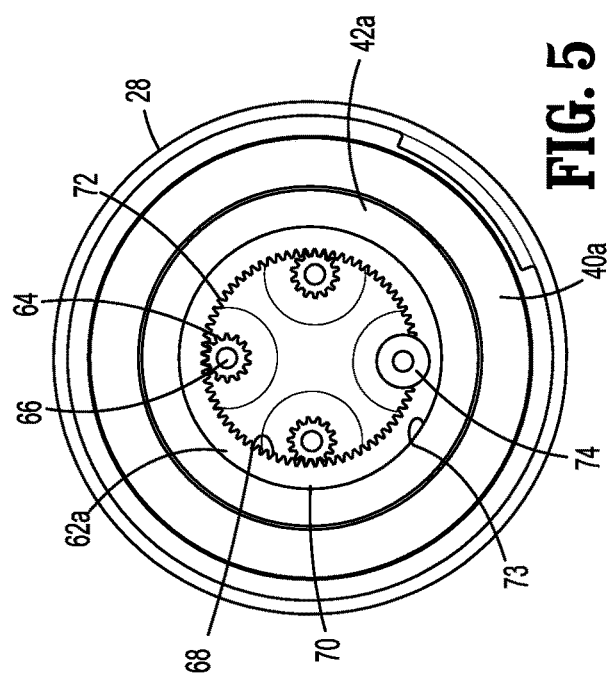
FIG. 5 is an end view of the instrument drive unit of FIG. 3, as seen from the top down.
Figure 6:
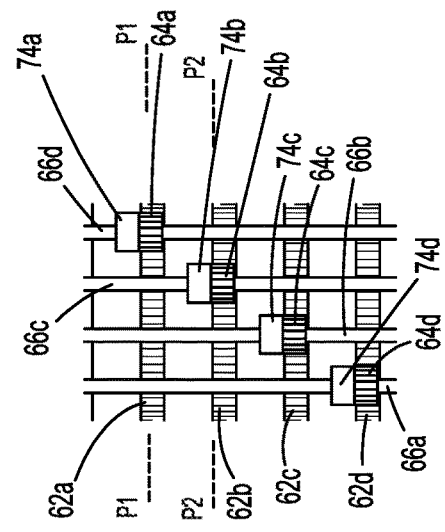
FIG. 6 is a schematic, side cross-sectional view of the instrument drive unit of FIG. 3, as taken through 6-6 of FIG. 3.

The ring gears 62a, 62d are vertically stacked within the motors 22. In particular, the ring gears 62a, 62d are coaxial along the central longitudinal axis "X" defined by the motors 22. As best shown in FIG. 5, each of the ring gears 62a, 62d has an outer periphery 70 adhered to an inner periphery 73 of a respective rotor 42, such that each ring gear and rotor pair (e.g., ring gear 62a and rotor 42a) rotate together relative to the corresponding stator 40a. Each ring gear 62a, 62d has gear teeth 68 extending from an inner periphery 72 thereof. The gear teeth 68 on the inner periphery 72 of each of the ring gears 62a, 62d interfaces with a corresponding drive gear 64, as will be described. In embodiments, each of the rings gears 62a, 62d may be constructed as a rotor 42 rather than being integrally connected with a rotor 42.

The drive shafts 66a, 66b, 66c, 66d extend longitudinally through the motors 22 and distally therefrom. The drive shafts 66 each have a distal end portion configured to operably couple to a driven member (not explicitly shown) of the surgical instrument 10. For example, the distal end portion of each of the drive shafts 66 may have a coupler (e.g., a gear) for coupling with a corresponding coupler of a driven member of the surgical instrument 10. Accordingly, upon bottom-loading of the electromechanical instrument 10 into the instrument drive unit 20, the distal end portions of the drive shafts 66 of the instrument drive unit 20 operably couple to the gears/couplers in a distal end of the main body portion (not shown) of the electromechanical instrument 10, such that a rotation of each drive shaft 66 rotates a correspondingly coupled driven member of the surgical instrument 10 to effectuate a discrete function of the surgical instrument (e.g., opening/closing of the end effector, articulation of the end effector, etc.)

The drive shafts 66 each have a drive gear 64 such as, for example, a spur gear, rotationally fixed thereabout. Each of the drive gears 64 are positioned at a discrete vertical location on their respective drive shaft 66, such that the drive gears 64 are vertically offset a selected distance from one another. Since the drive gears 64, in addition to being vertically offset, are also circumferentially spaced from one another, the drive gears 64 are offset from one another in all three dimensions. As mentioned above, the drive gears 64 each interface or intermesh with the gear teeth 68 on the inner periphery 72 of a corresponding ring gear 62 and receive torque therefrom originating from the respective rotor 42.

Each of the drive shafts 66 may have a nut 74a, 74b, 74c, 74d (collectively referred to herein as "74") fixed thereabout. The nuts 74 are disposed adjacent a corresponding drive gear 64 and fixed thereto, thereby fixedly coupling the drive gears 64 to the drive shafts 66. Each drive shaft 66 may further include a series of idler gears 76 rotatably disposed thereabout and vertically offset from one another. The series of idler gears 76 on each drive shaft 66 interface with a corresponding ring gear 62 to stabilize the plurality of drive shafts 66 within the plurality of electric motors 22.

In operation, the electromechanical instrument 10 is coupled to the instrument drive unit 20 by passing the main body portion of the electromechanical instrument 10 through the sleeve 28 of the instrument drive unit 20 in a proximal direction. With the main body portion of the electromechanical instrument 10 attached to the sleeve 28 of the instrument drive unit 28, the distal end portion of each of the drive shafts 66 interfaces with corresponding gears/couplers (not shown) in the proximal end of the main body portion of the electromechanical instrument 10.

With the electromechanical instrument 10 coupled to the instrument drive unit 20, to actuate a particular function of the surgical instrument 10, such as, for example, an opening or closing of an end effector of the surgical instrument 10, one of the electric motors 22 of the instrument drive unit 20, such as the first electric motor 22a, is activated via the control device 4 (FIG. 1). An activation of the first electric motor 22a includes supplying an electric current to the stator 40a thereof, which drives a rotation of the rotor 42a thereof. It is contemplated that the control device 4 or a processor (not shown) of the electric motor 22a generates a rotating magnetic field about the stator 40a to drive the rotation of the rotor 42a.

The first ring gear 62a rotates with the rotor 42a, which, in turn, rotates the first drive gear 64a. Since the first drive gear 64a is rotationally fixed about the first drive shaft 66a, and the distal end portion of the first drive shaft 66a is operably coupled to the proximal end of the first driven member of the surgical instrument 10 (FIG. 1), a rotation of the first drive gear 64a causes the first drive shaft 66a to rotate, thereby rotating the first driven member of the electromechanical instrument 10 to actuate an associated function of the surgical instrument 10.

To rotate the electromechanical instrument 10 about its longitudinal axis, the fifth electric motor 22e of the instrument drive unit 20 is activated by the control device 4 (FIG. 1). An activation of the fifth electric motor 22e includes supplying an electric current to the stator 40e thereof, which drives a rotation of the rotor 42e thereof. Rotation of the rotor 42e rotates the sleeve 28. Given that the electromechanical instrument 10 is non-rotationally supported in the sleeve 28, the electromechanical instrument 10 rotates with the sleeve 28 relative to the carriage 26 to change a rotational orientation of the electromechanical instrument 10.

The drive motors 22a, 22b, 22c, 22d may be configured to concurrently rotate the rotors 42a, 42b, 42c, 42d, and in turn the drive gears 64a, 64b, 64c, 64d, with the sleeve 28 rotation. This would prevent rotation of the drive shafts 66a, 66b, 66c, 66d relative to the ring gears 62a, 62b, 62c, 62d during rotation of the sleeve 28, which may otherwise occur if the drive gears 64a, 64b, 64c, 64d were allowed to rotate relative to the ring gears 62a, 62b, 62c, 62d during rotation of the sleeve 28. Conversely, the fifth motor 22e may be configured to counteract any torque output by the other four drive motors 22a, 22b, 22c, 22d to prevent the inadvertent rotation of the sleeve 28.

As can be appreciated, the instrument drive unit 20 described above improves usability of the surgical robotic system 1, reduces a foot-print of the overall system 1, improves safety architecture, reduces the time required to remove surgical instruments in case of an emergency, and simplifies the electronics used in the instrument drive unit 20.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use in a robotic surgical system, the instrument drive unit comprising:
    a carriage configured to be coupled to a robotic arm;
    a plurality of drive shafts rotationally supported in the carriage;
    a plurality of electric motors disposed about the plurality of drive shafts, wherein the plurality of electrical motors are vertically stacked within the carriage, each electric motor of the plurality of electric motors including a stator and a rotor disposed within the stator, wherein each stator is fixed relative to the carriage, and each rotor is rotatable relative to and within a corresponding stator; and
    a plurality of drive gears, each drive gear of the plurality of drive gears fixed to a corresponding drive shaft of the plurality of drive shafts and operably coupled to a corresponding rotor, wherein each rotor is configured to rotate a corresponding drive shaft of the plurality of drive shafts in response to an activation of a respective electric motor of the plurality of electric motors to actuate a function of an electromechanical surgical instrument.

2. The instrument drive unit according to claim 1, further comprising a plurality of ring gears, each ring gear of the plurality of ring gears fixed to a corresponding rotor and operably coupled to a corresponding drive gear of the plurality of drive gears.

3. The instrument drive unit according to claim 2, wherein each ring gear of the plurality of ring gears is concentrically disposed within a corresponding rotor, such that rotation of the rotor results in a rotation of the corresponding ring gear of the plurality of ring gears.

4. The instrument drive unit according to claim 2, wherein the plurality of ring gears are vertically stacked within the plurality of electric motors.

5. The instrument drive unit according to claim 2, wherein at least a first ring gear of the plurality of ring gears has gear teeth on an inner periphery thereof, wherein the gear teeth on the inner periphery of the first ring gear interface with a corresponding drive gear of the plurality of drive gears, and an outer periphery of the first ring gear is attached to an inner periphery of a corresponding rotor.

6. The instrument drive unit according to claim 1, wherein the plurality of drive gears are vertically offset from one another.

7. The instrument drive unit according to claim 1, wherein each drive shaft of the plurality of drive shafts has a distal end portion configured for interfacing with the electromechanical surgical instrument.

8. The instrument drive unit according to claim 1, wherein each drive shaft of the plurality of drive shafts has a series of idler gears rotatably disposed thereabout and vertically offset from one another, the series of idler gears interfacing with a corresponding ring gear to stabilize the plurality of drive shafts within the plurality of electric motors.

9. An instrument drive unit for use in a robotic surgical system, the instrument drive unit comprising:
    a carriage configured to be coupled to a robotic arm;
    a plurality of drive shafts rotationally supported in the carriage;
    a plurality of electric motors disposed about the plurality of drive shafts, each electric motor of the plurality of electric motors including a stator and a rotor disposed within the stator;
    a plurality of drive gears, each drive gear of the plurality of drive gears fixed to a corresponding drive shaft of the plurality of drive shafts and operably coupled to a corresponding rotor, wherein each rotor is configured to rotate a corresponding drive shaft of the plurality of drive shafts in response to an activation of a respective electric motor of the plurality of electric motors to actuate a function of an electromechanical surgical instrument; and
    a sleeve rotationally coupled to a distal end portion of the carriage and configured to non-rotationally retain the electromechanical surgical instrument,
    wherein in each electric motor of the plurality of electric motors:
        the stator is fixed within the carriage; and
        the rotor is disposed within the stator of each electric motor of the plurality of electric motors and non-rotatably coupled to the sleeve, wherein the rotor of each electric motor of the plurality of electric motors is configured to rotate the sleeve about a central longitudinal axis defined by the carriage.

10. An instrument drive unit for use in a robotic surgical system, the instrument drive unit comprising:
    a carriage configured to be coupled to a robotic arm;
    a plurality of drive shafts rotationally supported in the carriage;
    a plurality of electric motors disposed about the plurality of drive shafts, each electric motor of the plurality of electric motors including a stator and a rotor disposed within the stator;
    a plurality of drive gears, each drive gear of the plurality of drive gears fixed to a corresponding drive shaft of the plurality of drive shafts and operably coupled to a corresponding rotor, wherein each rotor is configured to rotate a corresponding drive shaft of the plurality of drive shafts in response to an activation of a respective electric motor of the plurality of electric motors to actuate a function of an electromechanical surgical instrument; and
    a plurality of ring gears, each ring gear of the plurality of ring gears fixed to a corresponding rotor and operably coupled to a corresponding drive gear of the plurality of drive gears,
    wherein a first electric motor of the plurality of electric motors, a first ring gear of the plurality of ring gears, and a first drive gear of the plurality of drive gears are operably coupled to one another and aligned along a first plane, and wherein a second electric motor of the plurality of electric motors, a second ring gear of the plurality of ring gears, and a second drive gear of the plurality of drive gears are operably coupled to one another and aligned along a second plane, vertically displaced from the first plane.

11. An instrument drive unit for use in a robotic surgical system, the instrument drive unit comprising:
a carriage configured to be coupled to a robotic arm;
a plurality of drive shafts rotationally supported in the carriage;
a plurality of electric motors disposed about the plurality of drive shafts, each electric motor of the plurality of electric motors including a stator and a rotor disposed within the stator;
a plurality of drive gears, each drive gear of the plurality of drive gears fixed to a corresponding drive shaft of the plurality of drive shafts and operably coupled to a corresponding rotor, wherein each rotor is configured to rotate a corresponding drive shaft of the plurality of drive shafts in response to an activation of a respective electric motor of the plurality of electric motors to actuate a function of an electromechanical surgical instrument; and
a plurality of ring gears, each ring gear of the plurality of ring gears fixed to a corresponding rotor and operably coupled to a corresponding drive gear of the plurality of drive gears, wherein the plurality of ring gears are independently rotatable relative to one another.

12. An instrument drive unit for use in a robotic surgical system, the instrument drive unit comprising:
a carriage configured to be coupled to a robotic arm;
a plurality of electric motors supported in the carriage, each electric motor of the plurality of electric motors including a stator and a rotor disposed within the stator; and
a plurality of drive shafts disposed within the plurality of electric motors and configured for interfacing with an electromechanical surgical instrument, each drive shaft of the plurality of drive shafts having a drive gear fixed thereabout, each drive gear being disposed at a discrete vertical location relative to one another, wherein each rotor is configured to rotate a corresponding drive gear in response to an activation of a respective electric motor of the plurality of electric motors to actuate a function of the electromechanical surgical instrument.

13. The instrument drive unit according to claim 12, further comprising a plurality of vertically stacked ring gears, each ring gear of the plurality of ring gears fixed to a corresponding rotor and operably coupled to a corresponding drive gear, such that each rotor is configured to rotate a corresponding drive gear in response to an activation of a respective electric motor of the plurality of electric motors to actuate a function of the electromechanical surgical instrument.

14. The instrument drive unit according to claim 13, wherein a first electric motor of the plurality of electric motors, a first ring gear of the plurality of ring gears, and a first drive gear attached to a first drive shaft of the plurality of drive shafts are operably coupled to one another and aligned along a first plane, and wherein a second electric motor of the plurality of electric motors, a second ring gear of the plurality of ring gears, and a second drive gear attached to a second drive shaft of the plurality of drive shafts are operably coupled to one another and aligned along a second plane, vertically displaced from the first plane.

15. The instrument drive unit according to claim 13, wherein each ring gear of the plurality of ring gears is concentrically disposed within a corresponding rotor, such that rotation of the rotor results in a rotation of the corresponding ring gear of the plurality of ring gears.

16. The instrument drive unit according to claim 12, further comprising:
a sleeve rotationally coupled to a distal end portion of the carriage and configured to non-rotationally retain the electromechanical surgical instrument; and
wherein in each electric motor of the plurality of electric motors:
the stator is fixed within the carriage; and
the rotor is disposed within the stator of each electric motor of the plurality of electric motors and non-rotatably coupled to the sleeve, wherein the rotor of each electric motor of the plurality of electric motors is configured to rotate the sleeve about a central longitudinal axis defined by the carriage.

17. The instrument drive unit according to claim 12, wherein each drive shaft of the plurality of drive shafts has a distal end portion configured for interfacing with the electromechanical surgical instrument.

18. The instrument drive unit according to claim 12, wherein each drive shaft of the plurality of drive shafts has a series of idler gears rotatably disposed thereabout and vertically offset from one another, the series of idler gears interfacing with a corresponding ring gear to stabilize the plurality of drive shafts within the plurality of electric motors.

* * * * *